United States Patent
Slater

[11] Patent Number: 5,810,799
[45] Date of Patent: Sep. 22, 1998

[54] DIAPER FOR A MALE WEARER

[76] Inventor: Elizabeth Slater, 42 Downing St., New York, N.Y. 10014

[21] Appl. No.: 622,796
[22] Filed: Mar. 27, 1996
[51] Int. Cl.⁶ ...................................................... A61F 13/15
[52] U.S. Cl. .......................................................... 604/385.1
[58] Field of Search .................................... 604/370, 378, 604/385.1, 369

[56] References Cited

U.S. PATENT DOCUMENTS

| | | |
|---|---|---|
| D. 352,151 | 11/1994 | Warnock . |
| 3,559,648 | 2/1971 | Mason . |
| 3,858,584 | 1/1975 | Johnson . |
| 3,926,189 | 12/1975 | Taylor ....................... 604/369 |
| 4,195,630 | 4/1980 | Connery et al. . |
| 4,414,971 | 11/1983 | Chung . |
| 4,501,587 | 2/1985 | Enloe ................................... 604/385.1 |
| 4,578,071 | 3/1986 | Buell .................................... 604/385.1 |
| 4,627,846 | 12/1986 | Ternström . |
| 4,675,012 | 6/1987 | Rooyakkers . |
| 4,778,459 | 10/1988 | Fuisz ..................................... 604/385.1 |
| 4,846,825 | 7/1989 | Enloe et al. . |
| 4,928,323 | 5/1990 | Nathan .................................. 604/385.1 |
| 4,950,263 | 8/1990 | Lewis ..................................... 604/385.1 |
| 5,037,413 | 8/1991 | Haque . |
| 5,074,853 | 12/1991 | Bryant . |
| 5,100,399 | 3/1992 | Janson et al. ......................... 604/385.1 |
| 5,146,874 | 9/1992 | Vidal . |
| 5,176,672 | 1/1993 | Bruemmer et al. ................... 604/385.1 |
| 5,207,662 | 5/1993 | James ..................................... 604/385.1 |
| 5,304,160 | 4/1994 | Igaue et al. . |
| 5,344,516 | 9/1994 | Tanji et al. ............................ 604/385.1 |
| 5,399,176 | 3/1995 | Chen ..................................... 604/385.1 |
| 5,417,680 | 5/1995 | Kimura et al. . |
| 5,429,622 | 7/1995 | Chung . |
| 5,447,506 | 9/1995 | Lindquist .............................. 604/385.1 |
| 5,601,543 | 2/1997 | Dreier et al. .......................... 604/385.1 |

FOREIGN PATENT DOCUMENTS

| | | | |
|---|---|---|---|
| 157649 | 10/1985 | European Pat. Off. ............ | 604/385.1 |
| 5228178 | 9/1993 | Japan .................................. | 604/385.1 |
| 93/03698 | 3/1993 | WIPO ................................. | 604/385.1 |
| 94/03137 | 2/1994 | WIPO ................................. | 604/385.1 |

OTHER PUBLICATIONS

ABE, Patents Abstracts of Japan, vol. 17. No. 685 (c11420 [6314] p. 45, Dec. 1993.

Primary Examiner—Robert A. Clarke
Attorney, Agent, or Firm—Kenyon & Kenyon

[57] ABSTRACT

A diaper having an absorbent barrier on the inside surface of the front of the diaper. The barrier is preferably in the form of a ridge or laterally elongated inverted pocket which extends from the inner surface of the absorbent inside portion. The barrier is positioned so that when the diaper is worn, it is either above the male's penis or is positioned to accommodate or accept at least a portion of the penis. The barrier is specially adapted to block inadvertent urinary discharge. In one embodiment, the barrier is an insert for a conventional diaper, the insert being secured to the inside of the diaper with tape or any other adhesive. In another embodiment, the barrier is integral with the interior of the diaper.

14 Claims, 14 Drawing Sheets

DIAPER FOR A MALE WEARER

FIELD OF THE INVENTION

The present invention relates to a diaper. More particularly, the present invention relates to a diaper constructed specifically for a male wearer.

Background of the Invention

It is generally well known that since males and females are anatomically different especially in terms of genitalia, it is desirable to provide a diaper that is especially designed with these anatomical differences in mind. U.S. Pat. No. 5,037,413 issued to Haque, for example, provides a pouch in a diaper for accommodating the male genitalia. This pouch provides extra room for the male genitalia thereby increasing comfort. For a female diaper wearer, the diaper features an extra absorbent pad provided in the area of the female genitalia, but without a pouch configuration. For both forms of the diaper, a padded ridge is provided in the area of the perineum, with absorbency in the ridge for preventing a flow of urine back from the genitalia to the anus.

U.S. Pat. No. 3,559,648 issued to Mason recognizes that males and females wet different areas of their respective diapers. Accordingly, a higher concentration of absorptive material is provided in the front portion of a diaper which is to be utilized by a male wearer while a higher concentration of absorptive material is provided in the central or rearward potion of the diaper which is to be utilized by a female wearer.

Other interesting hygienic cloth and diaper configurations designed strictly for male wearers are disclosed in U.S. Pat. No. 5,429,622 issued to Chung, U.S. Pat. No. 3,858,584 issued to Johnson, and U.S. Pat. No. 5,074,853 to Bryant. Referring first to the Chung patent, a hygienic cloth is disclosed which is worn under a diaper. The cloth comprises a hole in a soft absorbent cloth in order to separate the testicles from the groin area by allowing the testicles and the penis to extend out of the hole.

The Johnson patent discloses a diaper device for use with a male baby. The diaper has an opening through which the male member extends. An externally disposed removable absorbent container is detachably secured to the diaper in the region of the opening to collect urine for subsequent disposal. With this configuration, the diaper need only to be changed when the baby has a bowel movement.

Finally, the Bryant patent seeks to minimize a male wearer's exposure to wetness. The diaper is wrapped around the penis only, so that adjacent body parts are not in contact with the inside portion of the diaper.

The present invention addresses a problem not addressed by any of the above described patents. Often, parents are awakened in the middle of the night by the crying of baby boys rudely jarred awake because of the terrible discomfort of soaking wet pajamas. As is well known by these parents, infant males tend to urinate upwardly toward their abdomens. Conventional diapers simply do not prevent urine sprayed upwardly from escaping through the top of the diaper. The present invention addresses this problem by providing a urine barrier within a diaper. This barrier blocks the wetness from traveling upward and soaking the wearer's clothes.

SUMMARY OF THE INVENTION

The present invention provides a diaper having an absorbent barrier on the inside surface of the front of the diaper. The barrier is preferably in the form of a ridge or laterally elongated inverted pocket which extends from the inner surface of the absorbent inside portion. The barrier is positioned so that when the diaper is worn, it is either above the male's penis or is positioned to accommodate or accept at least a portion of the penis. In one embodiment, the barrier is an insert for a conventional diaper, the insert being secured to the inside of the diaper with tape or any other adhesive. In another embodiment, the barrier is integral with the interior of the diaper.

BRIEF DESCRIPTION OF THE DRAWINGS

The foregoing and other features of the present invention will be more readily apparent from the following detailed description of preferred embodiments taken in conjunction with the attached drawings wherein.

DETAILED DESCRIPTION

Figure 1:
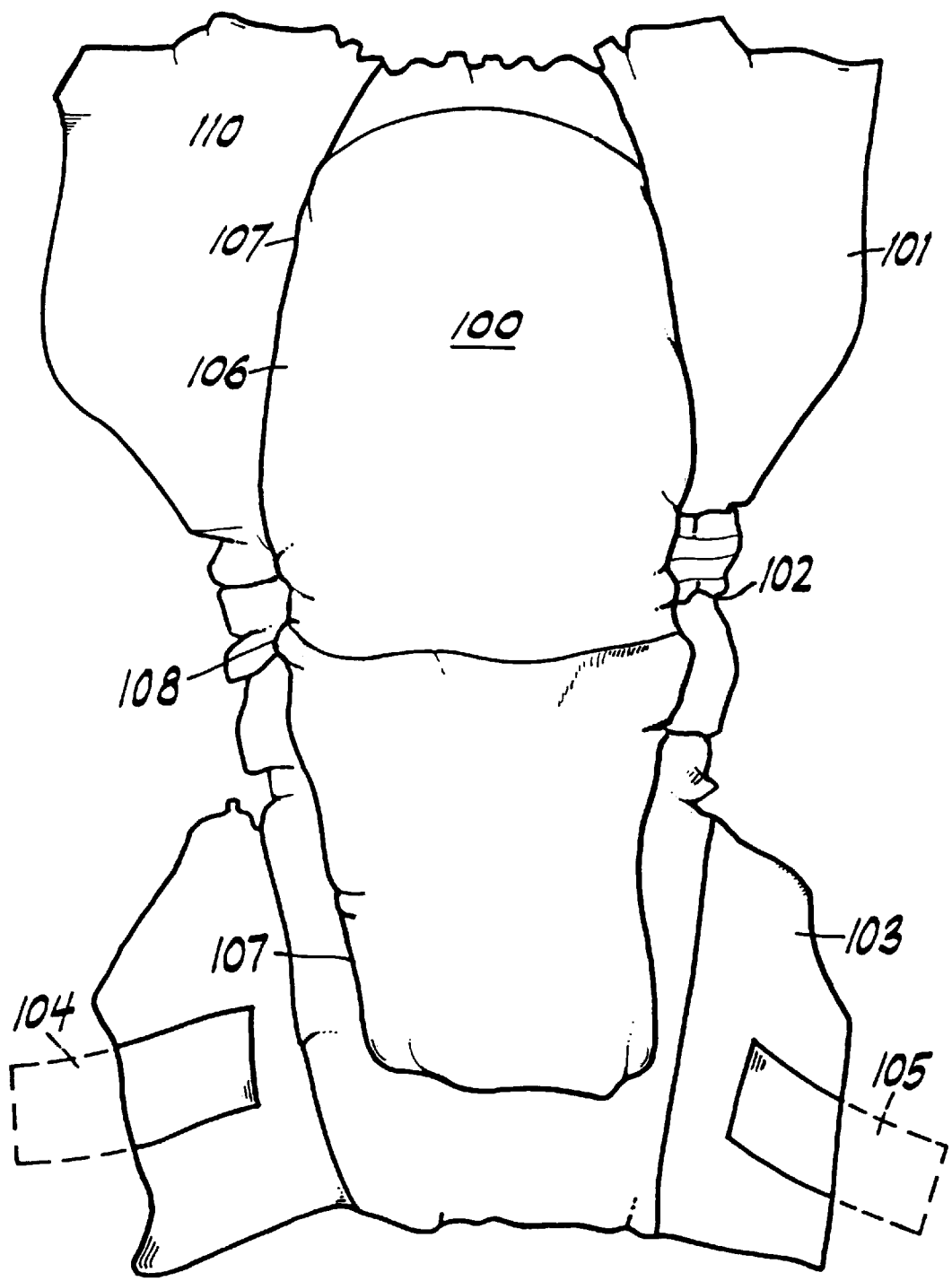
FIG. 1 is a plan view of the inside surface of a conventional disposable diaper.

Referring initially to FIG. 1, the inside surface 100 of a conventional prior art disposable diaper is shown. The diaper is comprised of a generally rectangular shaped liquid impermeable outer portion 110 having a front portion 101, a central portion 102, and a back portion 103. The long sides of the rectangle are preferably concave at the central portion 102 for comfortably accommodating the upper inside thigh of the wearer.

Tabs 104 and 105 are used to attach the back portion 103 of the liquid impermeable outer portion 110 to front portion 101 when the diaper is worn in the usual manner. Tabs 104 and 105 include an adhesive for securely fastening the diaper, but the diaper may also be secured with an eye and hook fastener such as Velcro®.

The diaper also includes an absorbent inner portion 106 having a generally rectangular shape. The inner portion 106, preferably adhered to the liquid impermeable outer portion 110 by known means, has a front portion 107, a central portion 108 and back portion 109 corresponding in position to the front portion 101, the central portion 102, and the back portion 103 respectively of the liquid impermeable outer portion 110. The inner portion 106 may be made of any absorbent material known in the art, including materials having a liquid absorbent core. For example, the inner portion 106 could comprise a liquid absorbent core surrounded by cloth material or could be comprised entirely of a thick padding of material.

Figure 2:
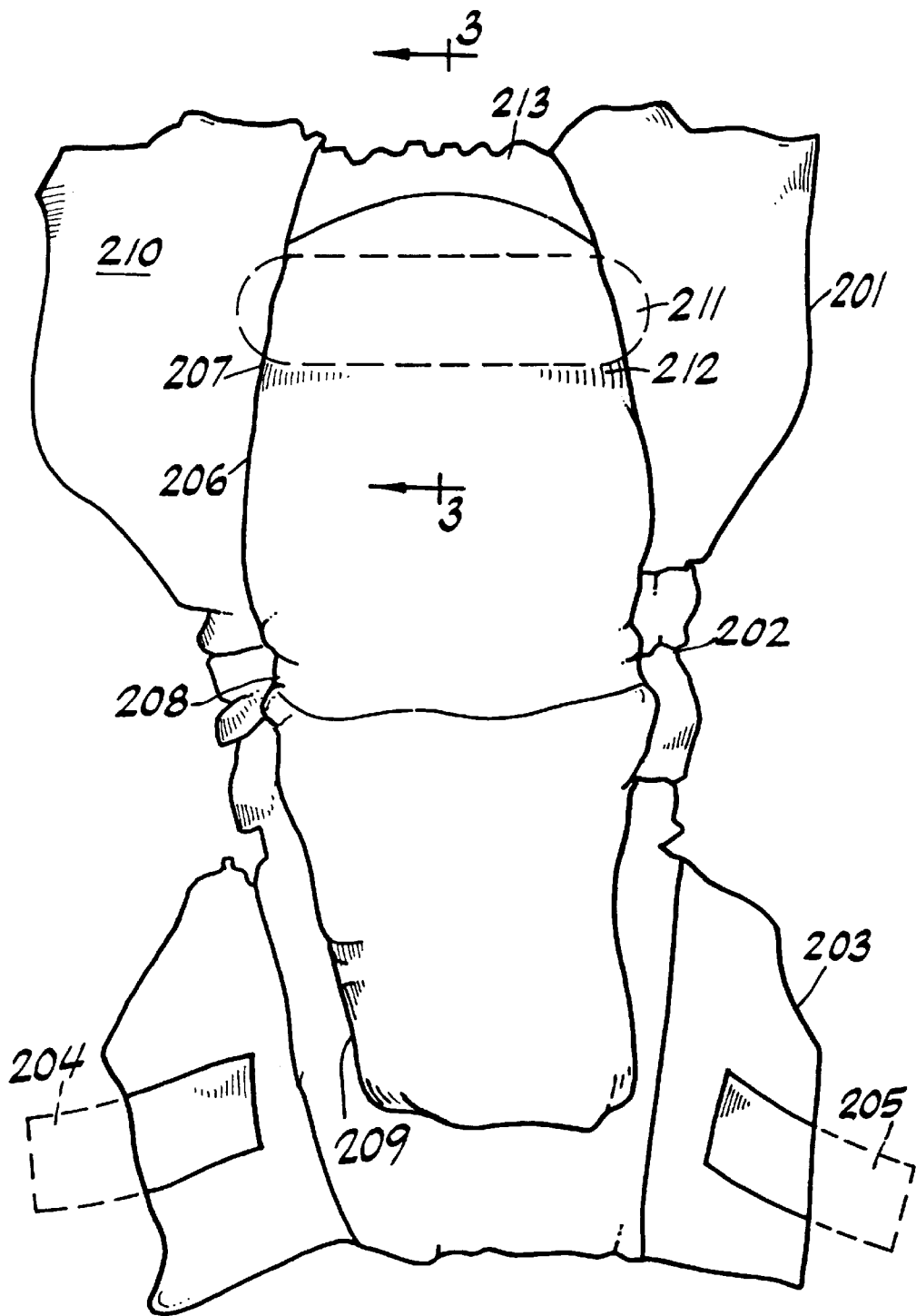
FIG. 2 is a plan view of the inside surface of one embodiment of the present invention.

Referring now to FIG. 2, the inside surface of a first embodiment of the present invention is illustrated. Those elements of FIG. 2 that correspond to similar elements of FIG. 1 have been similarly numbered (e.g., element 210 of FIG. 2 corresponds generally to element 110 of FIG. 1)—as is true for all the figures. The invention provides a barrier 211 adhered to or integral with the inside surface of the front portion 207 of inner portion 206. The barrier 211 of FIG. 2 is shown adhered to the front portion 207 of inner portion 206 with a faster 212. The fastener means can be, for example, an adhesive tape, Velcro, and the like. Alternatively, the barrier 211 can be sewn to the inside surface of the front portion 207 of inner portion 206. The barrier 211 is preferably comprised of an absorbent material and is positioned on the front portion 207 of inner portion 206 such that when the diaper is worn by a male, the barrier 211 is located above (or covering) the tip of the penis (as the natural inclination of the baby's penis is to point upward towards the baby's head when the baby is diapered). The barrier 211 extends from the inside surface of the inner portion 206 inwardly toward the wearer, i.e., it extends distally with respect to the outer portion 210, thus blocking urine sprayed in an upward direction from escaping beyond the top 213 of front portion 201 of liquid impermeable outer portion 210. The barrier 211 is preferably generally shaped as an oblong or rectangle, as illustrated in FIG. 2, to account for different positionings of the penis.

Figure 3:
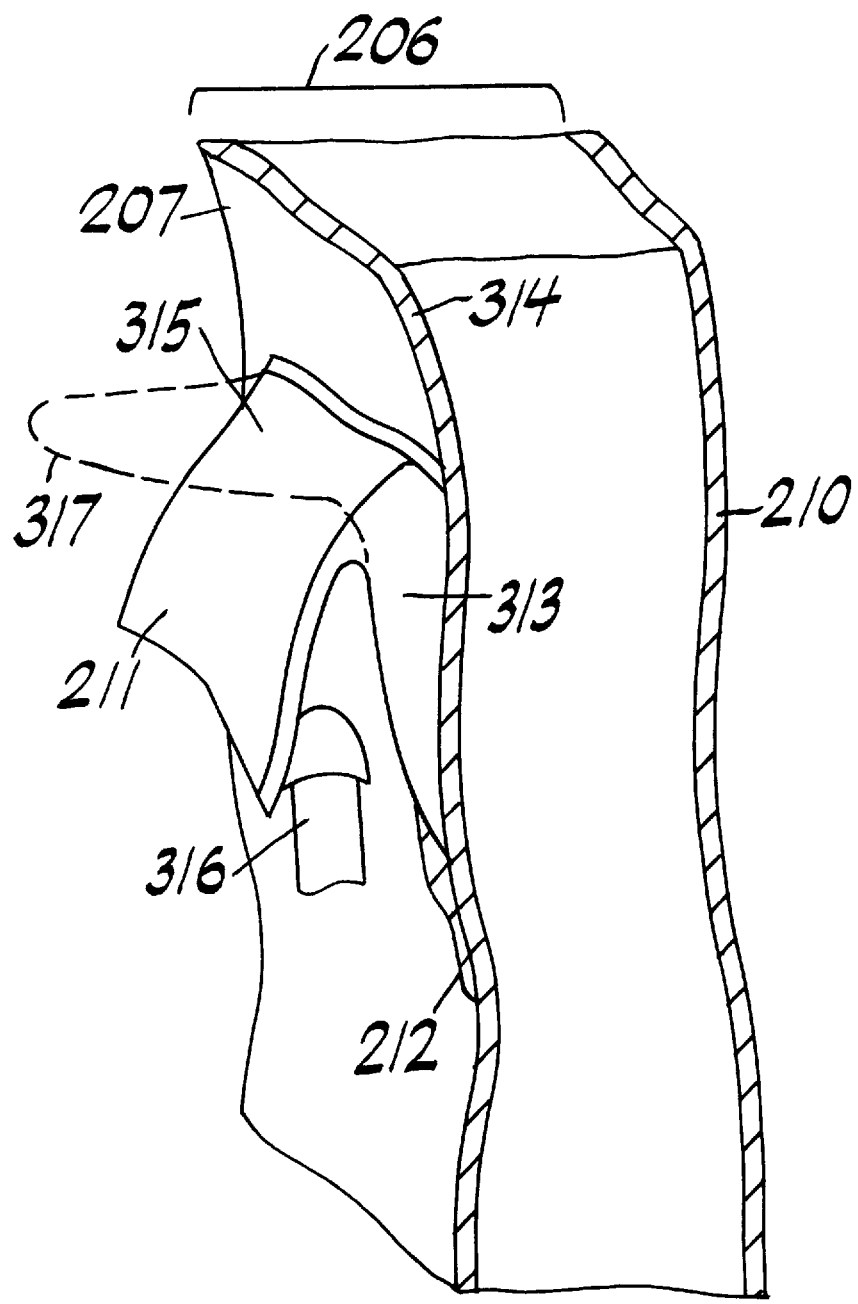
FIG. 3 is a sectional view taken along a line 3—3 of FIG. 2.

FIG. 3 illustrates a sectional view taken along a line 3—3 of FIG. 2, clearly showing the barrier 211 as part of an insert 313 for the diaper. The insert 313 is preferably formed of a single piece of absorbent material folded over. The portion of the insert 313 which is folded over and extends toward the wearer forms the barrier 211. The insert 313 is then adhered to the interior surface of the front portion 207 of inner portion 206 with an adhesive tape 212. FIG. 3 also clearly illustrates that the inner portion 206 includes a liquid permeable top sheet 314.

As can be understood by viewing both FIG. 2 and FIG. 3 concurrently, when the diaper is worn, the tip of the penis 316 fits below the fold 315 of insert 313 with the barrier 211 preferably partially covering it. As shown, the insert 313 with the barrier 311 is in the shape of an inverted pocket which comfortably accepts or accommodates the tip of the penis 316 when the penis is pointing approximately upwardly with respect to the wearer's head. It should be noted that the penis of a baby is inclined to point in a forward or upward position. This is especially true once a male baby is diapered; if the penis is not pushed intentionally downward it will in fact end up facing upward towards the baby's head causing the urine to leak out of the front of the diaper but for the present invention. In fact, even when the penis is pushed intentionally downward it inevitably switches direction with any small movement.

Barrier 211 may also extend generally perpendicularly to the inner portion 206 —shown in phantom form as element 317, thus being positioned completely above the tip of the penis.

Figure 4:
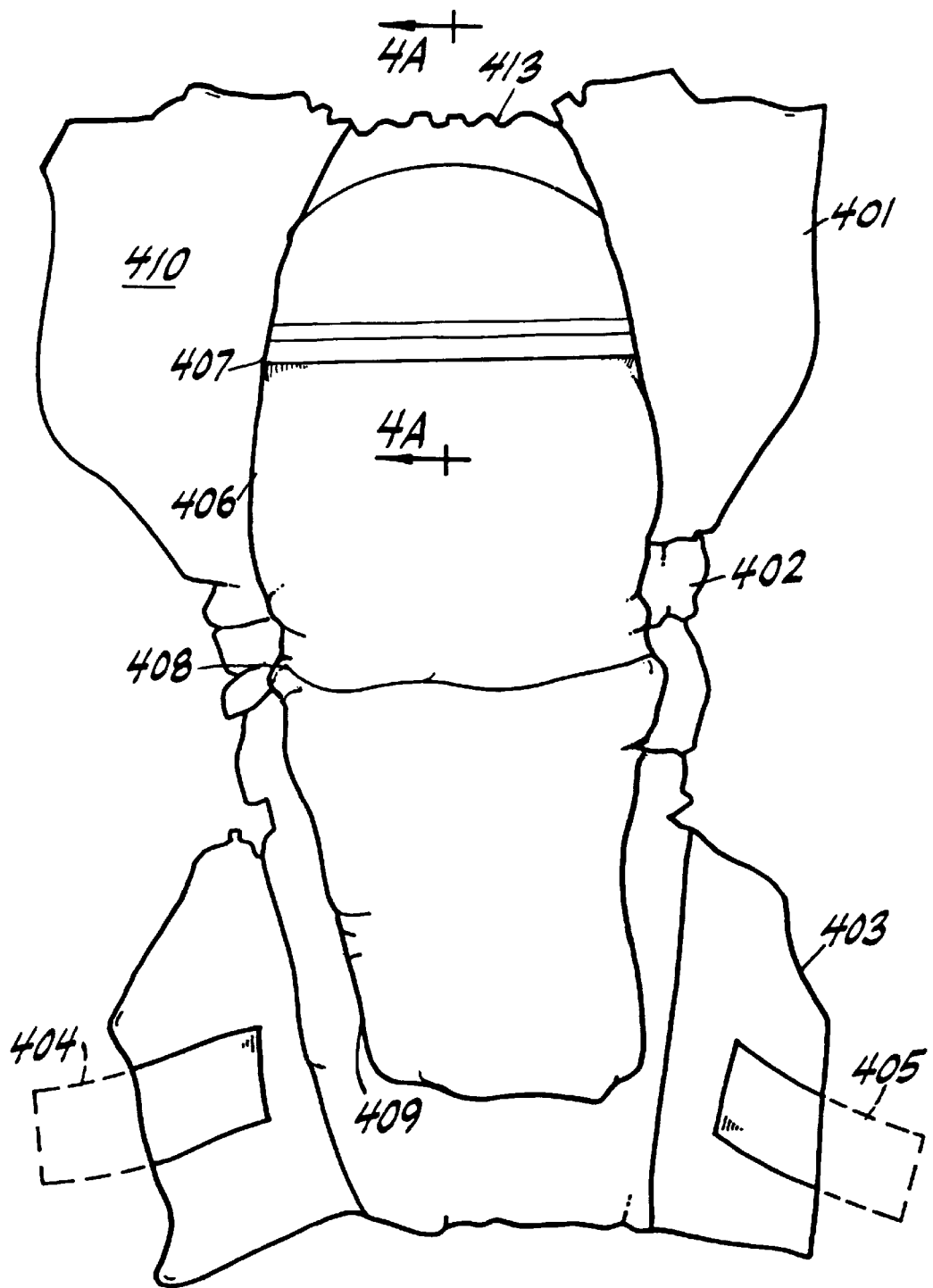
FIG. 4 is a plan view of the inside surface of a second embodiment of the present invention.
Figure 4A:
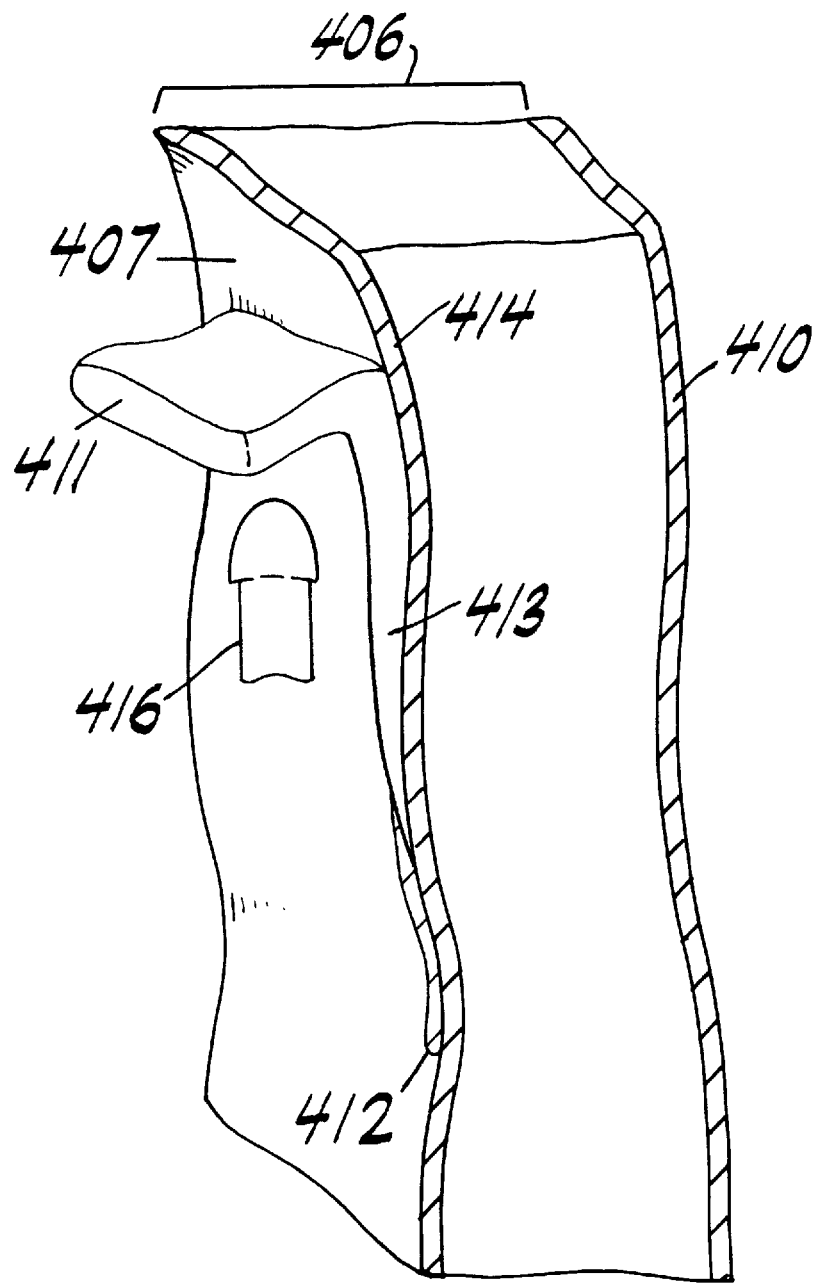
FIG. 4a is a sectional view taken along a line 4a—4a of FIG. 4.

FIGS. 4 and 4a illustrate another alternative embodiment of the barrier 411 of the present invention. As shown, barrier 411 is in the form of a ridge on the insert 413, preferably formed of absorbent material. The ridge form of barrier 411 preferably extends across at least some of the width (i.e., the short side of the rectangle) of the front portion 407 of the absorbent inner portion 406 and is positioned generally above the tip of the penis 416 when the diaper is worn.

Figure 5:
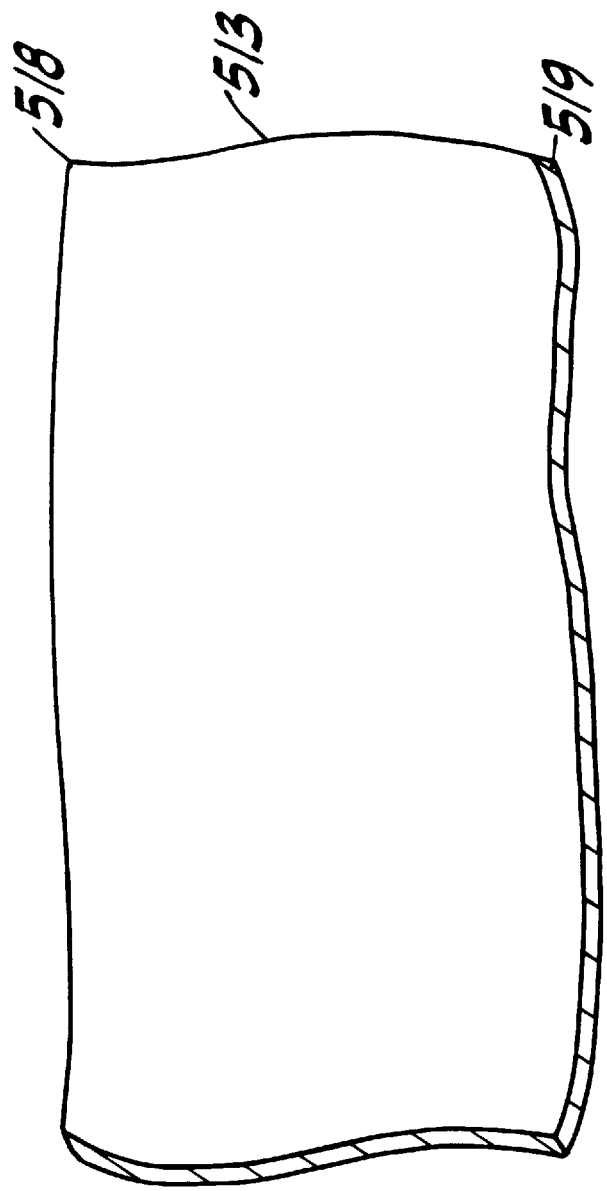
FIG. 5 is a plan view of the absorbent material forming the insert of the present invention.
Figure 6:
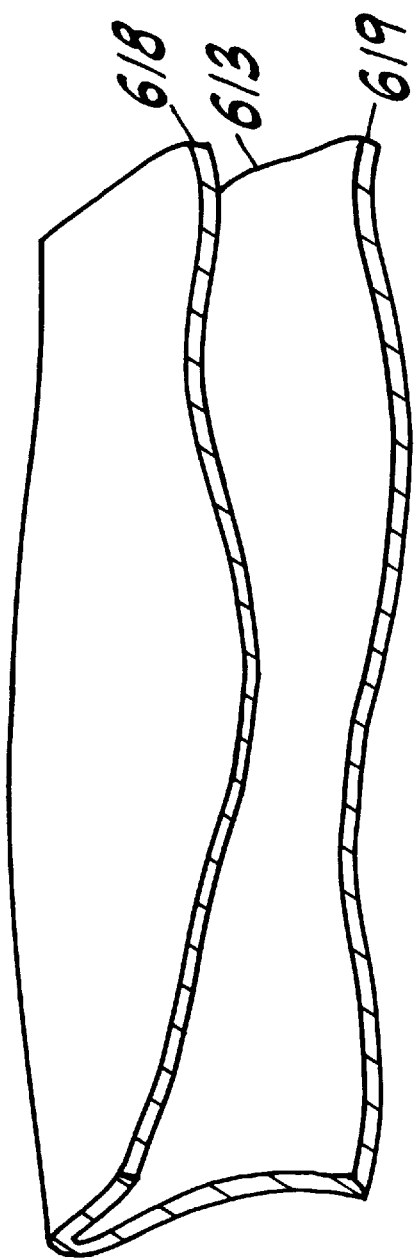
FIG. 6 is a perspective view of the completed diaper insert of the present invention.

FIGS. 5 and 6 illustrate one method of making the insert used in the embodiment illustrated in FIG. 3. FIG. 5 shows a single piece of absorbent material, in a generally rectangular shape, used for forming the insert 513 and having a top potion 518 and 519. The top portion 518 is folded toward the bottom portion 519, forming a pocket shaped insert 613 shown in FIG. 6.

Figure 7:
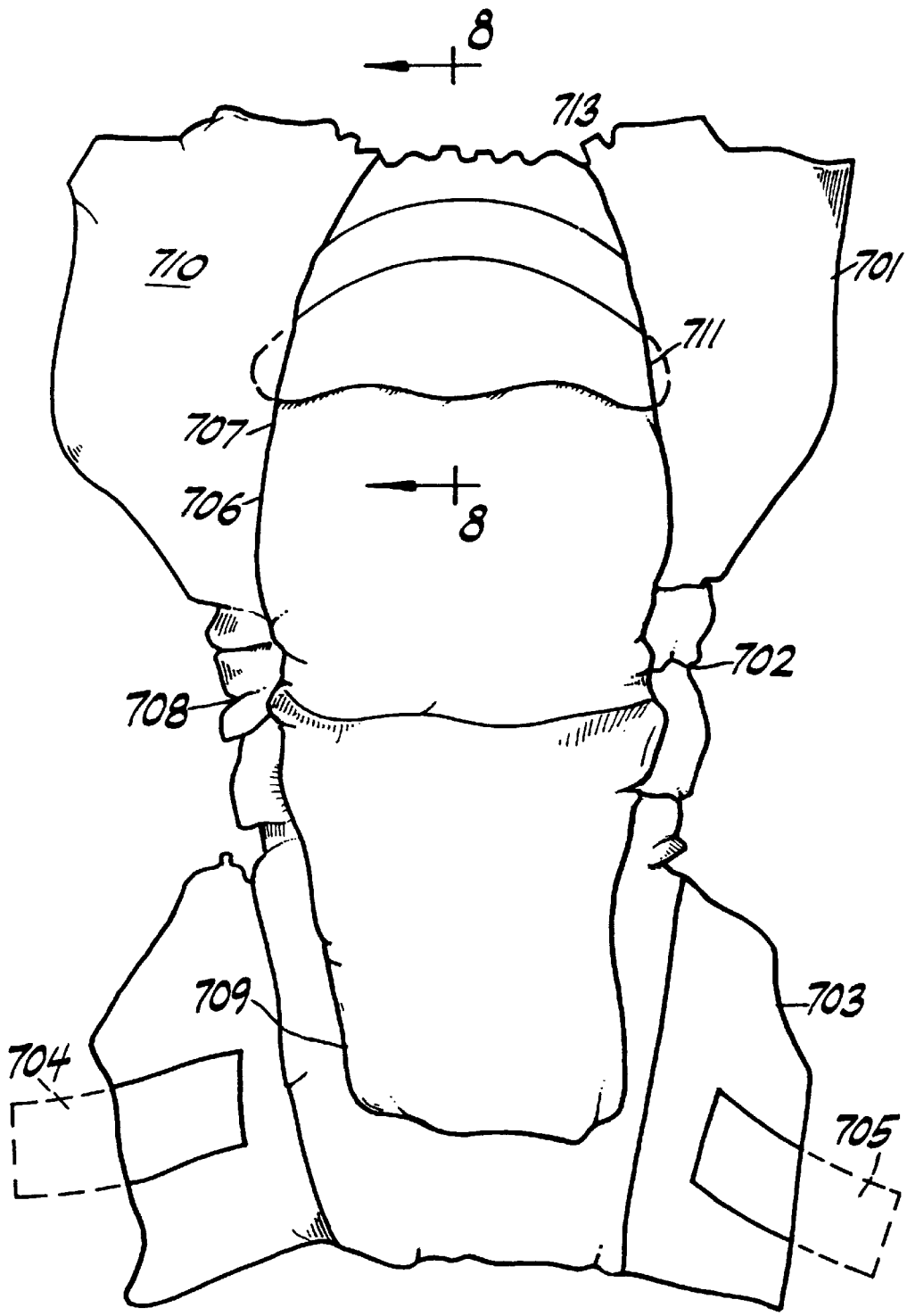
FIG. 7 is a plan view of the inside surface of an third embodiment of the present invention.
Figure 8:
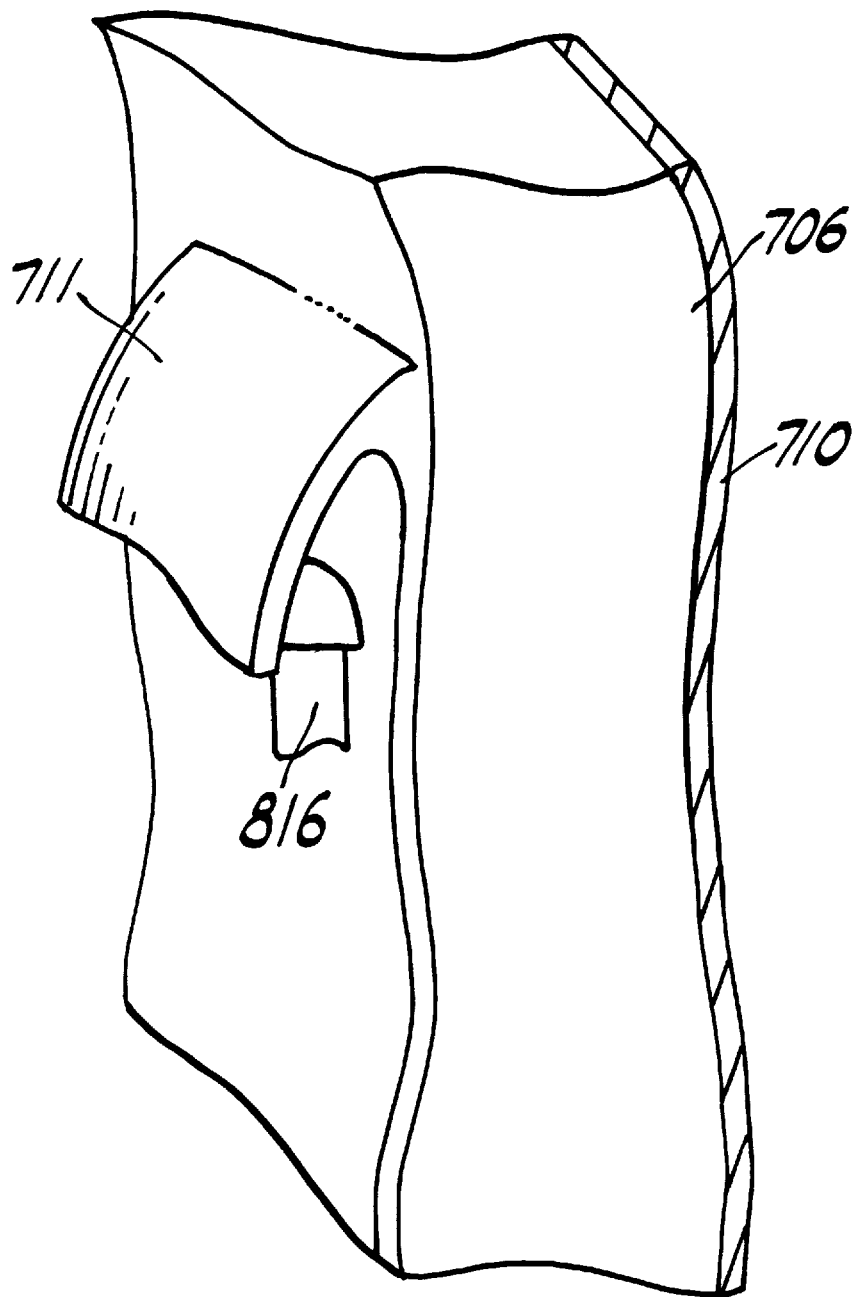
FIG. 8 is a sectional view taken along a line 8—8 in FIG. 7.

The embodiment of the invention illustrated in FIG. 7 is similar to that shown in FIGS. 2 and 3 except that the barrier 711 is integral with the front portion 707 of inner portion 706 rather than being a part of an added insert. Referring now to FIG. 8, a sectional view of the embodiment of FIG. 7 (taken along a line 8—8) is illustrated. As shown, the barrier 711 is integral with the inner portion 706 and extends in a direction toward the wearer. When worn by a male, the barrier 711 preferably partially covers the penis 816. As is the case with the embodiment of FIG. 2, the barrier 811 prevents urine which is sprayed upwardly (toward the head of the wearer) from escaping beyond the top 713 of front portion 701 of liquid impermeable outer portion 710.

Figure 9:
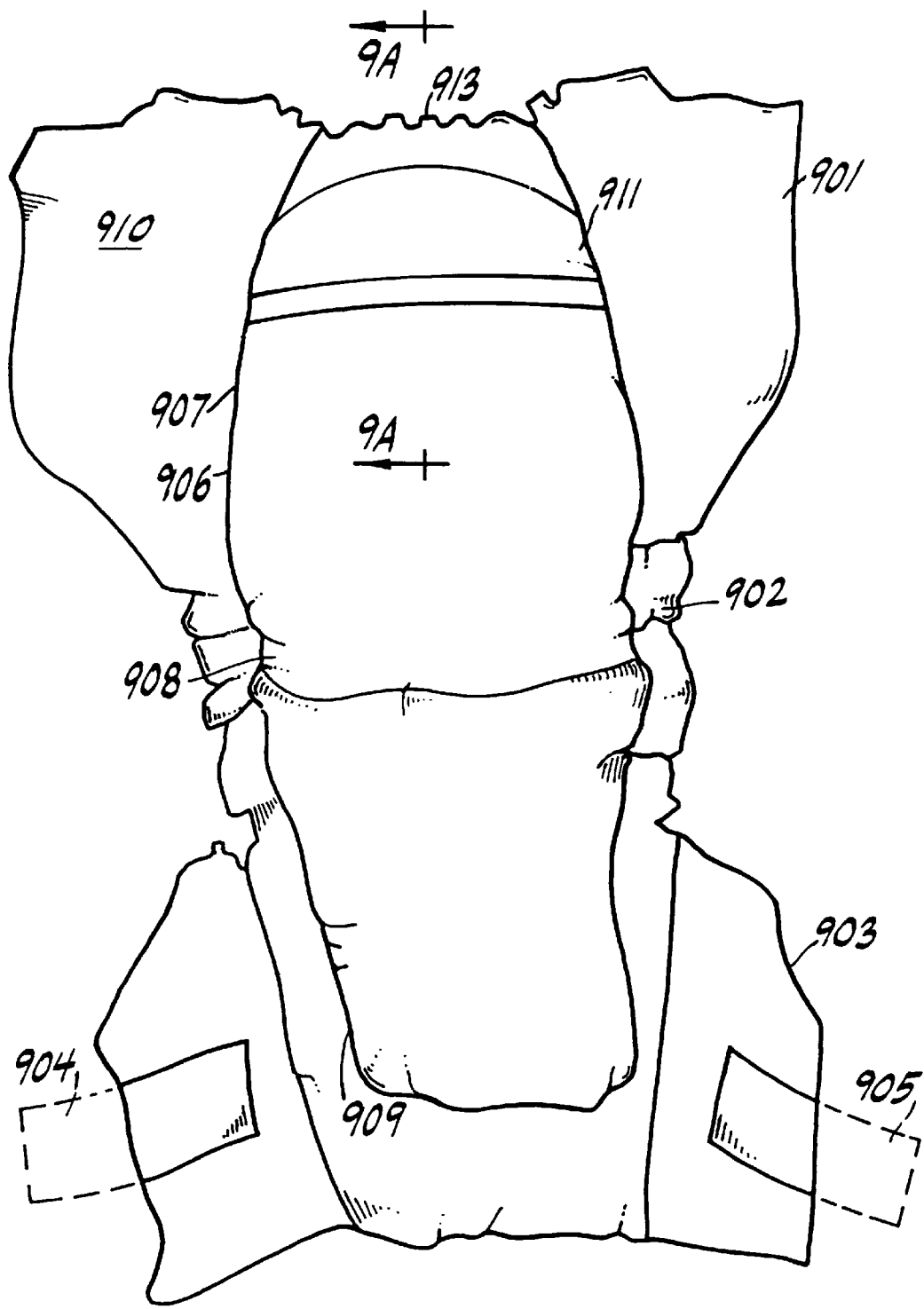
FIG. 9 is a plan view of the inside surface of a forth embodiment of the present invention.
Figure 9A:
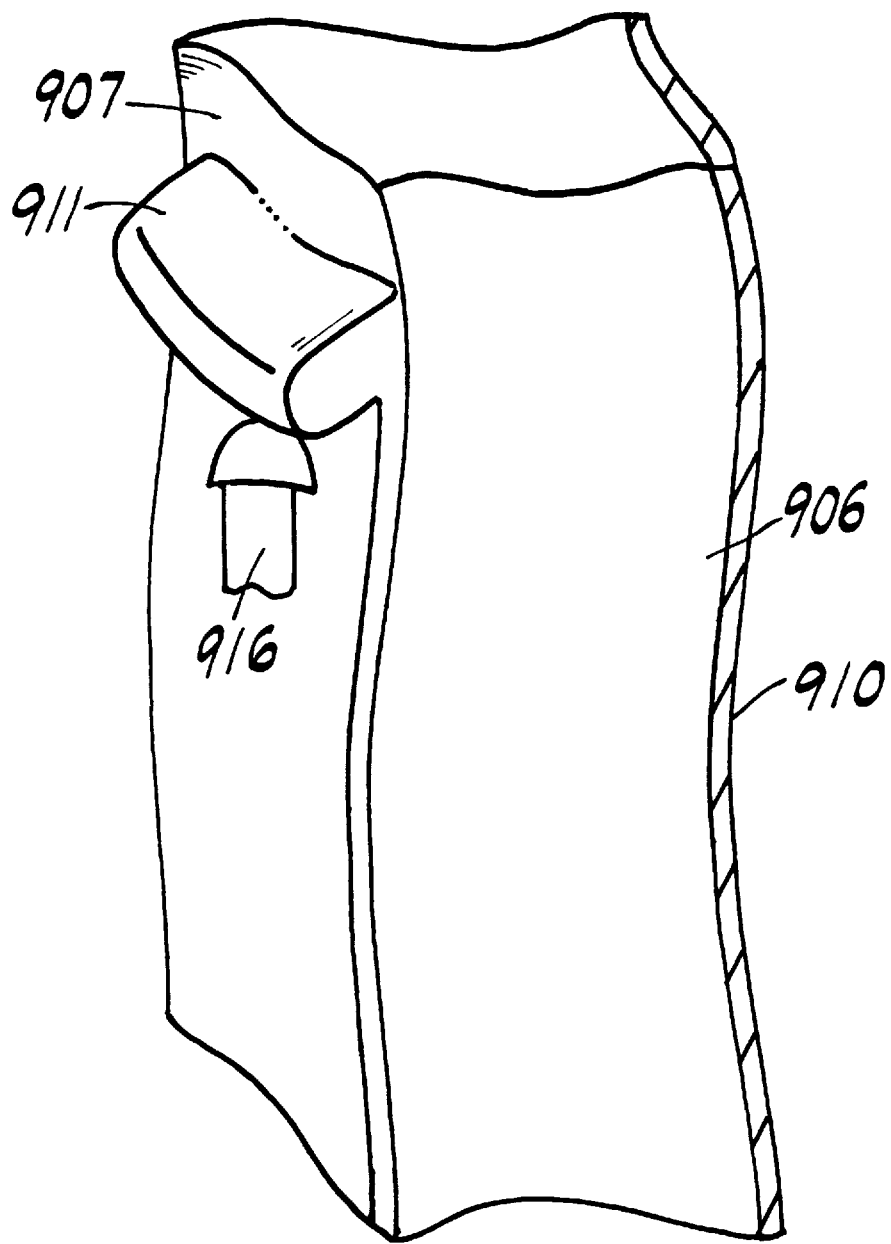
FIG. 9a is a sectional view taken along a line 9a—9a of FIG. 9.

FIGS. 9 and 9a illustrate yet another possible embodiment of the present invention. As shown, barrier 911 is a ridge formed on the inner surface of the front portion 907 of the absorbent inner portion 906. The ridge or barrier 911 is preferably formed of absorbent material. The ridge form of barrier 911 preferably extends across at least some of the width (i.e., the short side of the rectangle) of the front portion 907 of the inner portion 906 and is positioned generally above the tip of the penis 916 when the diaper is worn.

Figure 10:
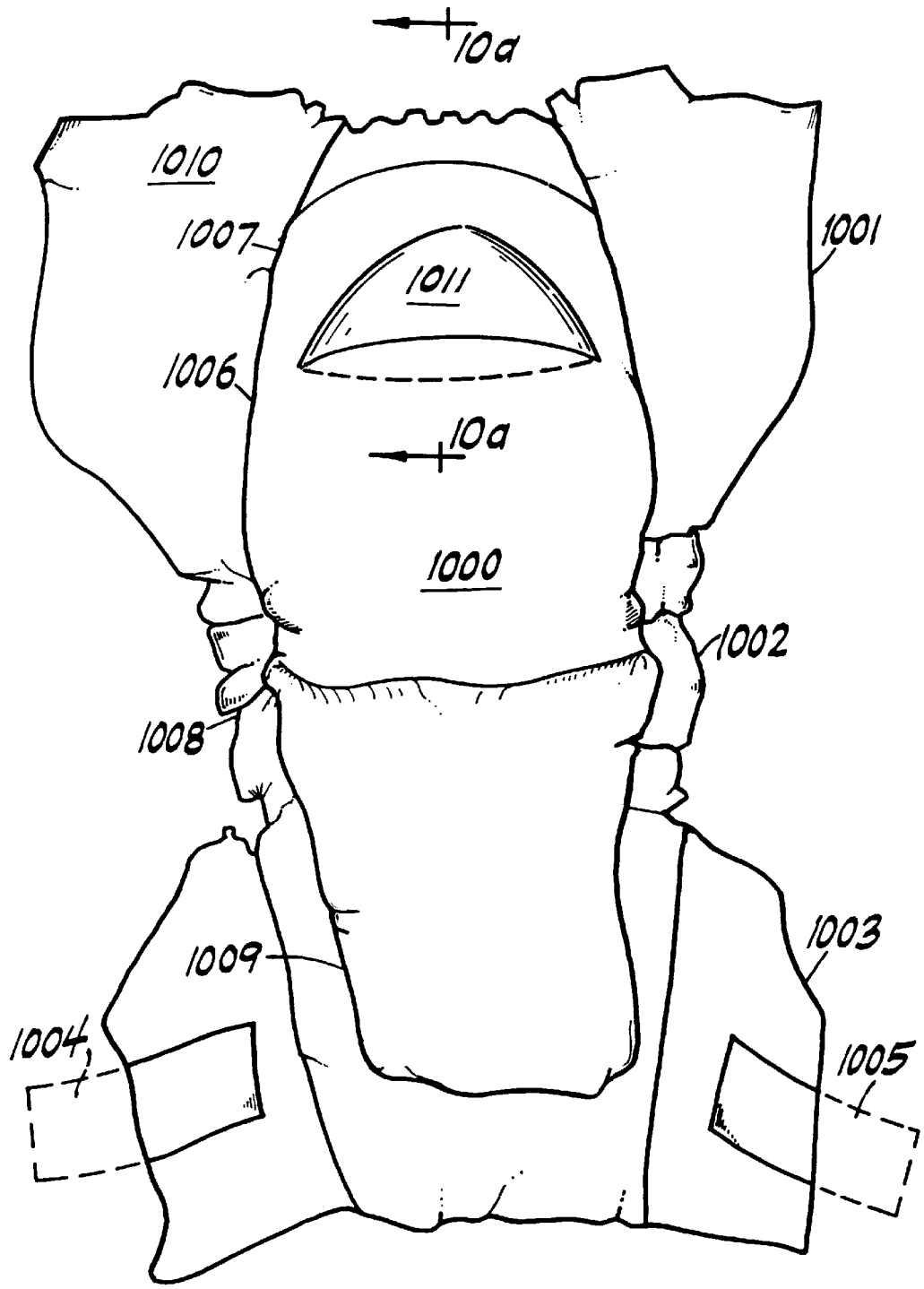
FIG. 10 is a plan view of the inside surface of a fifth embodiment of the present invention.
Figure 10A:
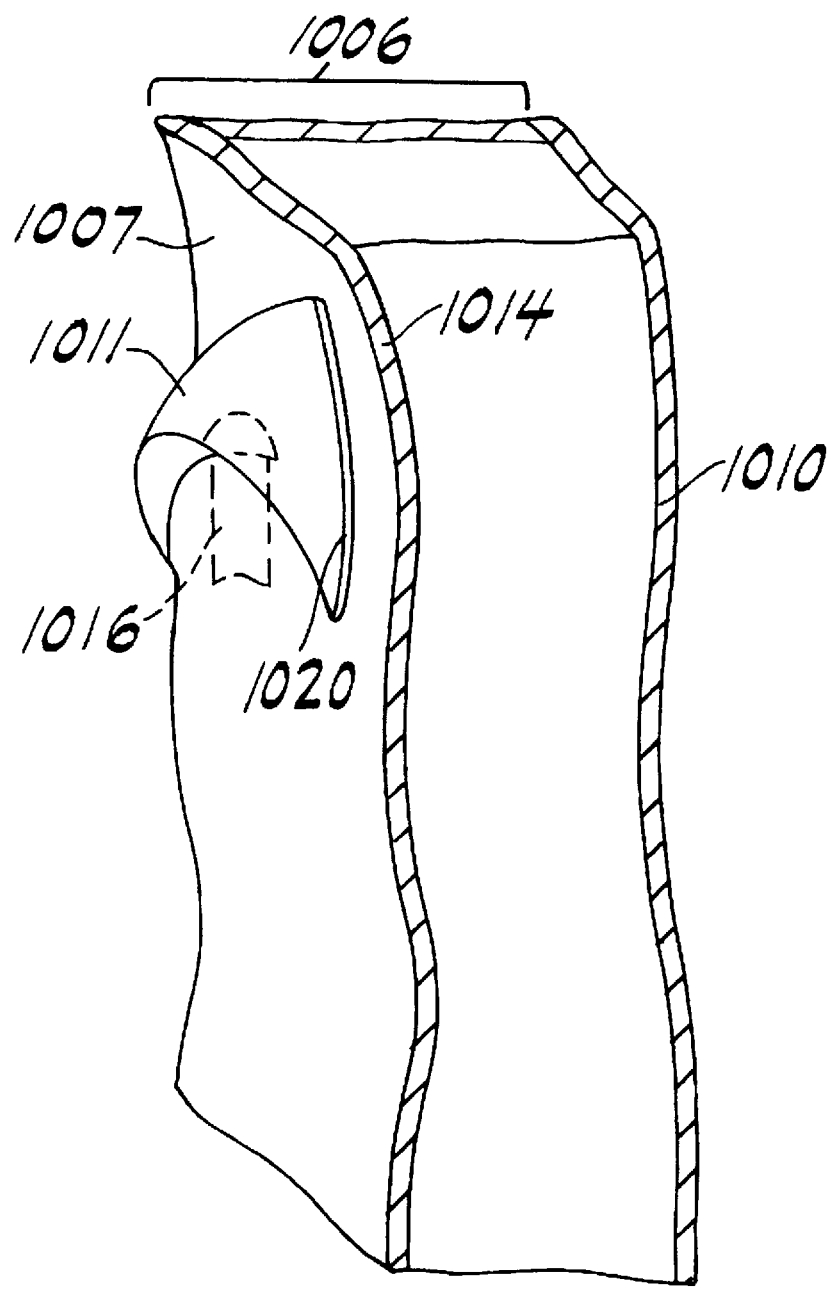
FIG. 10a is a sectional view taken along a line 10a—10a of FIG. 10.

Referring now to FIGS. 10 and 10a, yet another embodiment of the present invention is illustrated. In this embodiment, barrier 1011 is a substantially triangular shaped pouch or pocket, preferably made from an absorbent material. As illustrated, the pouch or barrier 1011 is large enough not to constrict the penis 1016 yet acts as a barrier by accepting the upper part of the penis and preventing urine from spraying upward toward the wearer's head.

On the back side of the pouch or barrier 1011 is an adhesive 1020 or other fastening means for securing the pouch to the front potion 1007 of inner portion 1006. Alternatively, the pouch or barrier 1011 may be integral with the front portion 207 of inner portion 206.

Figure 11:
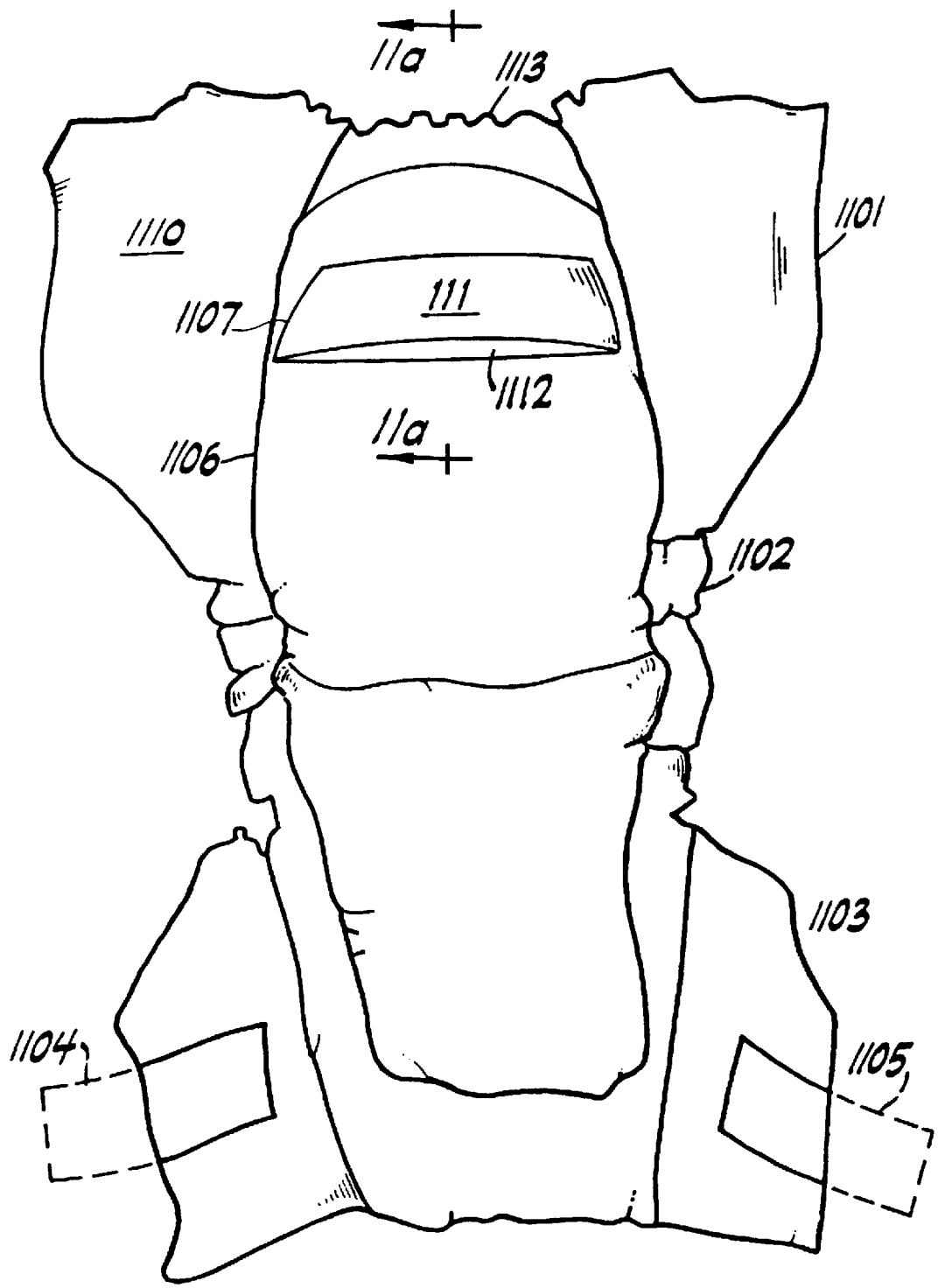
FIG. 11 is a plan view of the inside surface of a sixth embodiment of the present invention.
Figure 11A:
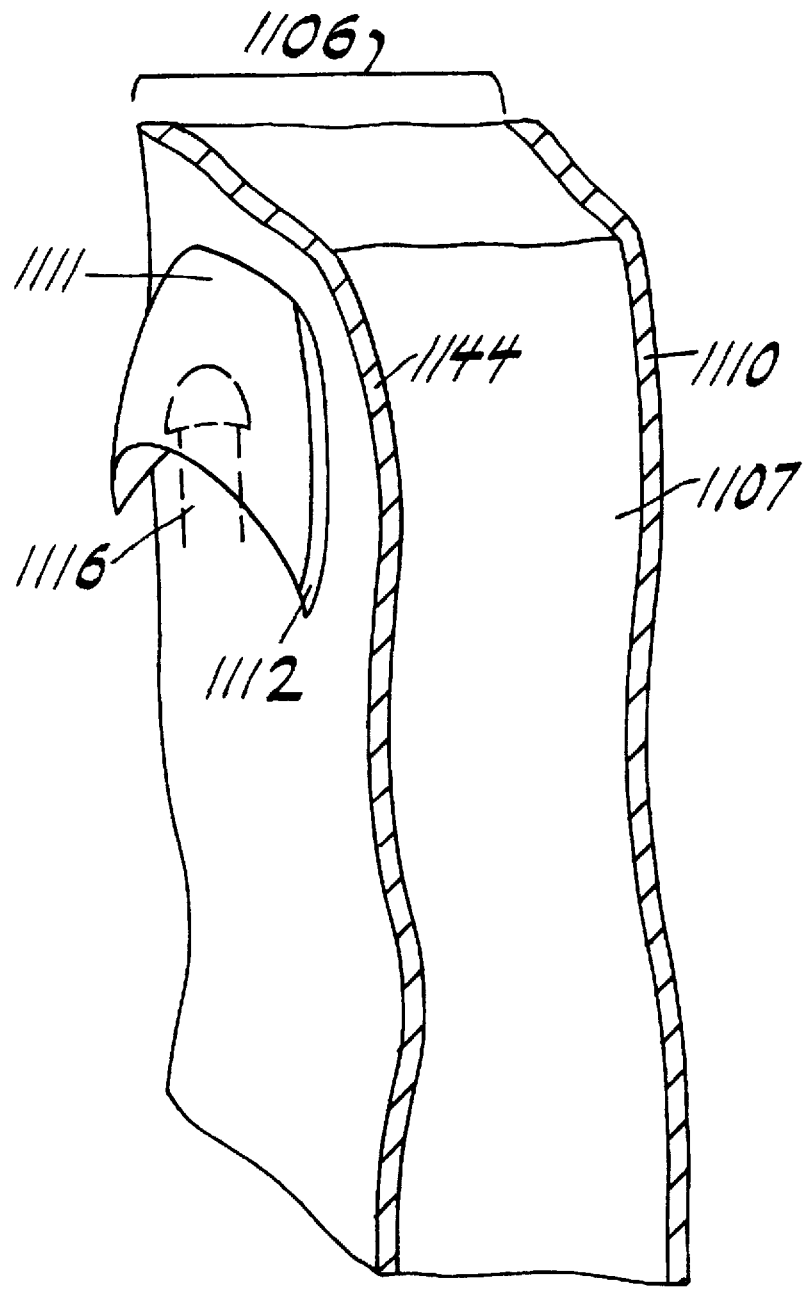
FIG. 11a is a sectional view taken along a line 11a—11a of FIG. 11.

FIGS. 11 and 11a illustrate another embodiment of the present invention. Here, barrier 1111 is a pouch or pocket that is substantially trapezoidal in shape. The back side of barrier 1111 may be secured to the front portion 1107 of inner portion 1106 with an adhesive 1020 or the like. The pouch or barrier 1111 may alternatively be integral with the front portion 207 of inner portion 206.

As indicated above, the present invention is directed to providing a means for keeping upwardly spayed urine from escaping the confines of the diaper. While the present invention has been particularly shown and described with reference to preferred embodiments thereof, it will be understood by those skilled in the art that various changes in form and details may be made therein without departing from the spirit and scope of the invention.

What is claimed is:

1. A diaper for an infant male, the diaper including a front section and a back section, the front section corresponding to a front of the infant male, and the back section corresponding to a back of the infant male, comprising:

an outer liquid impermeable portion having a length; and an inner absorbent portion extending for a least a portion of the length of said outer portion, said inner portion having an inner surface, a width, a front portion, a central portion, and a back portion, said inner surface being distal to said outer portion, said front portion corresponding to the front section and comprising a barrier positioned on said inside surface such that when said diaper is worn by the infant male, said barrier is positioned above a penis of the infant male; and at least one fastener connected to the back section, the fastener for securing the back section to the front section when said diaper is worn by said infant male;

wherein said barrier is a raised ridge extending across at least a portion of the width of said inner portion and comprised of an absorbent material, and wherein said barrier extends toward the infant male when said diaper is worn by the infant male, the barrier blocking upwardly sprayed urine from escaping from the diaper.

2. A diaper for an infant male, the diaper including a front section and a back section, the front section corresponding to a front of the infant male, and the back section corresponding to a back of the infant male, comprising:

an outer liquid impermeable portion having a length; and an inner absorbent portion extending for a least a portion of the length of said outer portion, said inner portion having an inner surface, a width, a front portion, a central portion, and a back portion, said inner surface being distal to said outer portion, said front portion corresponding to the front section and comprising a barrier positioned on said inside surface such that when said diaper is worn by the infant male, said barrier is positioned above a penis of the infant male; and at least one fastener connected to the back section, the fastener for securing the back section to the front section when said diaper is worn by said infant male;

wherein said barrier extends approximately perpendicularly from said inner surface of said front portion so that when said diaper is worn by the infant male, the barrier extends toward the infant male and is comprised of an absorbent material, the barrier blocking upwardly sprayed urine from escaping from the diaper.

3. The diaper of claim 2 wherein said barrier is integral with said inner portion.

4. The diaper of claim 2 wherein said barrier is attached to said inside surface with an adhesive.

5. A diaper for infant male, the diaper including a front section and a back section, the front section corresponding to a front of the infant male, and the back section corresponding to a back of the infant male, comprising:

an outer liquid impermeable portion having a length;

an inner absorbent portion extending for a least a portion of the length of said outer portion, said inner portion having an inner surface, a width, a front portion, a central portion, and a back portion, said inner surface being distal to said outer portion, said front portion corresponding to the front section and comprising a barrier positioned on said inside surface such that when said diaper is worn by the infant male said barrier is positioned above a penis of the infant male, the barrier blocking upwardly sprayed urine from escaping from the diaper; and at least one fastener connected to the back section, the fastener for securing the back section to the front section when said diaper is worn by said infant male;

wherein said barrier is an inverted pocket and is comprised of an absorbent material.

6. The diaper of claim 5 wherein said inverted pocket is triangular in shape.

7. The diaper of claim 5 wherein said inverted pocket is trapezoidal in shape.

8. A diaper for an infant male, the diaper including a front section and a back section, the front section corresponding to a front of the infant male, and the back section corresponding to a back of the infant male, comprising:

an outer liquid impermeable portion having a length;

an inner absorbent portion extending for a least a portion of the length of said outer portion, said inner portion having an inner surface, a width, a front portion, a central portion, and a back portion, said inner surface being distal to said outer portion, the front portion corresponding to the front section, wherein said front portion includes an inverted pocket positioned on said inside surface which receives at least a portion of a penis of the infant male when the diaper is worn by the infant male, and blocks upwardly sprayed urine from escaping from the diaper; and at least one fastener connected to the back section, the fastener for securing the back section to the front section when the diaper is worn by the infant male.

9. The diaper of claim 8 wherein said inverted pocket is made of an absorbent material.

10. The diaper of claim 8 wherein said inverted pocket extends across at least a portion of the width of said inner portion.

11. The diaper of claim 8 wherein said inverted pocket is integral with said inner portion.

12. The diaper of claim 8 wherein said inverted pocket is attached to said inner surface with an adhesive.

13. The diaper of claim 8 wherein said inverted pocket is substantially triangular in shape.

14. The diaper of claim 8 wherein said inverted pocket is substantially trapezoidal in shape.

* * * * *